(12) United States Patent
Tow

(10) Patent No.: US 9,884,318 B2
(45) Date of Patent: Feb. 6, 2018

(54) MULTI-AXIS, MULTI-PURPOSE ROBOTICS AUTOMATION AND QUALITY ADAPTIVE ADDITIVE MANUFACTURING

(71) Applicant: Adam Perry Tow, Boca Raton, FL (US)

(72) Inventor: Adam Perry Tow, Boca Raton, FL (US)

( * ) Notice: Subject to any disclaimer, the term of this patent is extended or adjusted under 35 U.S.C. 154(b) by 513 days.

(21) Appl. No.: 13/761,272

(22) Filed: Feb. 7, 2013

(65) Prior Publication Data

US 2013/0209600 A1 Aug. 15, 2013

Related U.S. Application Data

(60) Provisional application No. 61/633,433, filed on Feb. 10, 2012, provisional application No. 61/741,368, filed on Jul. 18, 2012, provisional application No. 61/689,963, filed on Jun. 18, 2012.

(51) Int. Cl.
| | |
|---|---|
| *B01L 3/02* | (2006.01) |
| *B33Y 30/00* | (2015.01) |
| *B29C 64/209* | (2017.01) |
| *B29C 64/171* | (2017.01) |
| *B29C 64/295* | (2017.01) |
| *B29C 64/393* | (2017.01) |
| *G01N 35/10* | (2006.01) |
| *B33Y 50/02* | (2015.01) |
| *B29C 64/106* | (2017.01) |

(52) U.S. Cl.
CPC ............. *B01L 3/02* (2013.01); *B29C 64/171* (2017.08); *B29C 64/209* (2017.08); *B29C 64/295* (2017.08); *B29C 64/393* (2017.08); *B33Y 30/00* (2014.12); *G01N 35/1011* (2013.01); *B29C 64/106* (2017.08); *B33Y 50/02* (2014.12)

(58) Field of Classification Search
CPC ............ B29C 67/0051; B29C 67/0059; B29C 67/0085; B29C 64/106; B29C 64/171; B29C 64/209; B29C 64/255; B29C 64/295; B29C 64/393; B33Y 30/00; B33Y 50/02
USPC ....................................................... 425/375
See application file for complete search history.

(56) References Cited

U.S. PATENT DOCUMENTS

| | | | | |
|---|---|---|---|---|
| 3,553,371 | A * | 1/1971 | Suenaga ..................... | 358/502 |
| 5,784,279 | A * | 7/1998 | Barlage et al. ............. | 700/119 |
| 6,280,784 | B1 * | 8/2001 | Yang et al. .................. | 426/231 |
| 6,405,095 | B1 * | 6/2002 | Jang et al. ................... | 700/118 |
| 7,625,198 | B2 | 12/2009 | Lipson et al. | |
| 2004/0217186 | A1 * | 11/2004 | Sachs et al. .................. | 239/11 |
| 2005/0139123 | A1 * | 6/2005 | Fujiwara .................... | 106/31.48 |
| 2006/0111807 | A1 * | 5/2006 | Gothait et al. .............. | 700/119 |

(Continued)

*Primary Examiner* — Edmund Lee
*Assistant Examiner* — Ninh Le

(57) ABSTRACT

A system and method for using multi-axis deposition tool heads on a machine such as a three dimensional fabrication device like a 3D Printer, for novel automation and additive manufacturing techniques which offer increased output product quality and fabrication speed by introducing a novel cartridge and deposition systems and techniques. The system allows a plurality of materials, some reacted or mixed by the device, to be extruded through a deposition head, which may adaptively (and automatically) change shape and lumen size to accommodate different path widths and shapes. The cartridge system may employ pellets which may be comprised of a plurality of materials and/or colors.

12 Claims, 35 Drawing Sheets

(56) References Cited

U.S. PATENT DOCUMENTS

2009/0170230 A1* 7/2009 Kidu et al. ............... 438/35
2010/0208016 A1* 8/2010 Menchik et al. ........... 347/86
2012/0241993 A1   9/2012 Lipton et al.

* cited by examiner ized applications. The present invention can thereby make additive manufacturing more practical and may result in a drastic improvement in output product quality. In one aspect of the present invention disclosed and claimed herein, a pellet based cartridge system is used, whereby unwieldy material spools are eliminated and multiple colors of the same material (or several different materials) can be easily combined in output products. Pellets can be provided in many different shapes or sizes. In another aspect of the present invention, by using a dynamic deposition head, the size and shape of the deposition tool are adjusted according to the character of the output product, allowing for much higher output product resolution. In another aspect of the present system, a large flat surface could be created in as little as one deposition path, by mechanically (and preferably, automatically) adjusting or switching the shape and/or size of the deposition head appropriately. A narrow surface of the same output product could be created at precise resolution (i.e., matching path width to output product surface width) by adjusting the deposition head extrusion opening's size and/or shape.

MULTI-AXIS, MULTI-PURPOSE ROBOTICS AUTOMATION AND QUALITY ADAPTIVE ADDITIVE MANUFACTURING

REFERENCE TO RELATED APPLICATIONS

This applicant claims the benefit of U.S. Provisional Application Ser. No. 61/633,433, filed Feb. 10, 2012 and incorporated by reference herein; U.S. Provisional Application Ser. No. 61/741,368, filed Jul. 18, 2012 and incorporated by reference herein; U.S. Provisional Application Ser. No. 61/689,963, filed Jun. 18, 2012 and incorporated by reference herein.

BACKGROUND OF THE INVENTION

1. Field of the Invention

The present invention relates to additive manufacturing and automation systems and techniques, such as three dimensional fabrication.

2. Background

There have been many developments in additive manufacturing in recent years, and three dimensional fabrication or "printing" systems have become an increasingly practical means of manufacturing organic and inorganic materials from a digital model. For clarity, three dimensional fabricators may be referred to as an additive manufacturing device or 3D Printer. A description of many such fabrication systems and recent developments in the art can be found in U.S. Pat. No. 7,625,198 to Lipson et al. and the patents and publications referenced therein.

Currently, many additive manufacturing devices employ a filament based system in which the device extrudes a pre-made, mono-color (often plastic) filament through a constrained, heated deposition head. Devices of this nature use large, mass produced spools or "cartridges" (i.e. small, enclosed spools) of plastic filament. Such spools tend to become tangled and make existing additive manufacturing systems clumsy and predisposed to undesirable results. Such systems practically limit the additive manufacturing devices to single color/material output products. By extruding the filament through a "static" deposition head, the shape and size of the liquefied material is constrained. The same problem occurs in additive manufacturing devices which do not use solid filaments, but instead fluid lines. Therefore, upon manufacturing an output product with a flat surface, the deposition head must make several passes and deposit several "paths" of the same size/shape. This process leads to output products which are clearly identified to have been created by additive manufacturing, due to the zigzagged appearance of flat surfaces resulting from having a single, static deposition lumen shape/size, which must be passed over a flat surface in several paths.

Due to the inherent complexities of additive manufacturing and the shortcomings in currently known techniques, existing additive manufacturing systems may fail to achieve optimal levels of performance and product quality. Current systems are generally limited to mono-material and mono-color prints and cannot adapt well to a user's desired material properties and physical appearance. In particular, it would be desirable to have additive manufacturing systems and techniques that do not result in output products that have noticeable imperfections or are otherwise inferior to products from non-additive manufacturing systems and techniques.

SUMMARY OF THE INVENTION

The shortcomings of the prior art can be overcome and additional advantages can be provided with the additive manufacturing systems and techniques described herein.

The deposition head may, for example, be guided by a control unit receiving instructions from a fabrication command unit (which may be a computer) running either a locally-stored or server-based fabrication software application. The computer may be integrated into a fabrication device or connected to the fabrication device via a wireless connection such as Bluetooth, WLAN, NFC or other wireless communication technologies, or a wired connection such as Ethernet, USB, FireWire, serial or parallel connection, or other wired communication technologies.

Some of the features provided by the system of the present disclosure are described as follows:

A three dimensional fabricator having a control unit for receiving instructions from a fabrication command unit and operating a material deposition tool head, a cartridge exchange bay for receiving material cartridges with the material deposition tool head being configured to deposit a plurality of different materials or colors provided by one or more material cartridges from the cartridge exchange bay, and a build surface for receiving material deposited by the material deposition tool head, such that the control unit can operate the material deposition tool head to deposit a plurality of different materials or colors on to the build surface to form a three dimensional structure according to a prescribed order and pattern. Additionally, the fabricator can include a mixing or fusing chamber to attach, react, or combine different materials or colors to create prescribed combinations. Additionally, the fabricator can utilize pellet based material provided by the one or more material cartridges, filament based material provided by the one or more material cartridges, and/or fluid based material provided by the one or more material cartridges. Additionally, the fabricator can have a gating mechanism to control the dispensation of material from each of the cartridges.

A three dimensional fabricator having a control unit for receiving instructions from a fabrication command unit and operating a material deposition tool head, a cartridge bay for receiving material cartridges, a build surface for receiving material deposited by the material deposition tool head, and a material chamber to mix or fuse a plurality of materials or colors for deposition on the build surface by the material deposition tool head to form a three dimensional structure according to a prescribed order and pattern. Additionally, the plurality of materials or colors can be attached sequentially by the material chamber, such that deposition of one material or color by the material deposition tool head can be immediately followed by deposition of another material or color. Additionally, the plurality of materials or colors can be combined by the material chamber to create a hybrid material or color, such that the hybrid material or color can be deposited by the material deposition tool head. Additionally, the fabricator's mixing chamber can mix or fuse pellet based material, filament based material and/or fluid based material. Additionally, the fabricator's mixing chamber can mix or fuse material with a dye or reactive agent.

A three dimensional fabricator having a control unit for receiving instructions from a fabrication command unit and operating a material deposition tool head, a plurality of interchangeable deposition tips, a build surface for receiving material deposited by the material deposition tool head, such that the control unit can operate the material deposition tool head to selectively use one of the plurality of interchangeable deposition tips to deposit material onto the build surface in different shapes or sizes to form a three dimensional structure according to a prescribed order and pattern. Additionally, the plurality of interchangeable tips can be attached to the material deposition tool head at the same time. Additionally, one or more interchangeable tips can be attached to the deposition tool head at any one time. Additionally, the tips can be stored in a controlled environment with regulated temperature, or other environmental control. Additionally, the tips can be disposable, and disposed automatically or manually.

A three dimensional fabricator having a control unit for receiving instructions from a fabrication command unit and operating a material deposition tool head, a build surface for receiving material deposited by the material deposition tool head, and one or more tips of adjustable shape or size that can be used by the material deposition tool head to deposit material onto the build surface in different shapes or sizes to form a three dimensional structure according to a prescribed order and pattern. Additionally, one or more tips can be manually, mechanically, electronically or magnetically adjusted to a different shape or size.

Embodiments of the present invention may be referred to as Quality Adaptive Additive Manufacturing, which includes a system and techniques for creating output products comprised of a multiplicity of materials at greater quality and resolution than traditional methods. Some embodiments of the invention use an input material in pellet form, and several materials (or colors of the same material) may be deposited sequentially onto a build surface to create a multi-color and/or multi-material output product. Whether through raw material in the form of pellets, fluids, or filaments, etc., or transformed as such within the device, the use of a mixing chamber allows for material to be fused sequentially, mixed, reacted, or dyed, according to the desired properties, (e.g., color or mechanical properties). By using a dynamically adaptive deposition tip, surfaces may be fabricated more quickly using fewer deposition paths leading to less visual indication an output product has been manufactured via additive manufacturing equipment. Whether the solid pellet component of the Quality Adaptive Additive Manufacturing technique or semi-solid and/or semi-liquid materials are being extruded, the system's dynamically adaptive deposition head will help increase output product quality and speed of manufacture by reducing the number of deposition paths required to create an output product. The system is capable of interchanging and even disposing of tips used to deposit or withdraw material. The present invention has many embodiments, some of which are described herein, and others which should be apparent to the reader or inferred from what is taught herein.

DETAILED DESCRIPTION OF THE PREFERRED EMBODIMENT(S)

Figure 1:
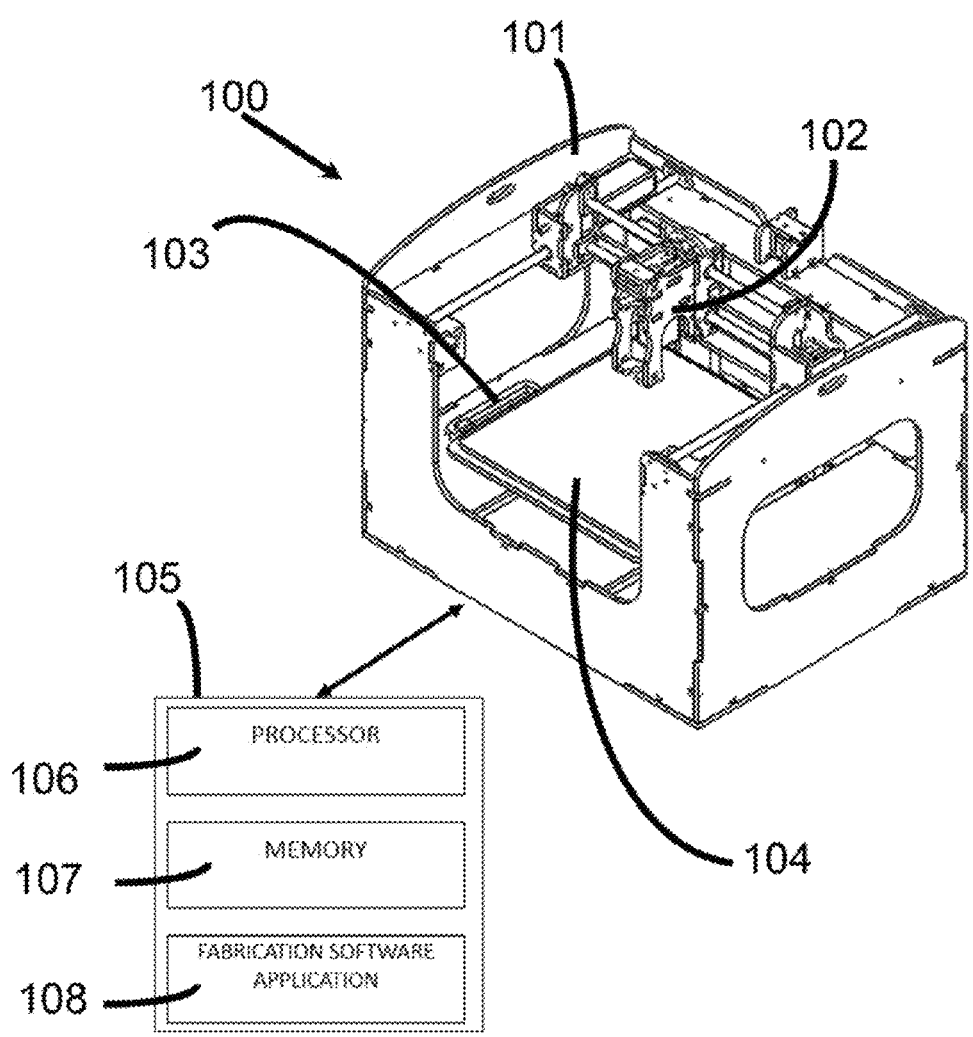
FIG. 1 is a perspective view of a three dimensional fabricator.

In order to provide some background regarding three dimensional fabricating systems and illustrate common components in such devices that may be used in connection with the present invention, FIG. 1 provides a perspective view of a prior art three dimensional fabricating system. Fabrication system 100 includes fabricator 101 with material deposition tool head 102 (also referred to herein as deposition tool or deposition head), control unit 103 having one or more actuators and sensors configured to control operating characteristics of material deposition tool 102, and build tray (i.e., build surface) 104. Fabrication command unit 105 may be coupled to fabricator 101 as a component physically inside fabricator 101, or it may be coupled as an external device (e.g., computer) via a wired or wireless connection.

Fabrication command unit 105 includes processor 106, memory 107, and fabrication software application 108 that can be stored in memory 107 and executed by processor 106. It should be appreciated that control unit 103 of fabricator 101 may be configured to receive instructions from fabrication command unit 105 such that fabricator 101 can fabricate an output product on build surface 104 from materials dispensed by material deposition tool 102.

The fabricated output product can be a three dimensional structure comprising a plurality of deposition layers. Material deposition tool 102 typically deposits material in viscous form and the material can be designed to solidify after being deposited to form an output product on build surface 104. Alternatively the material may require a separate curing process to solidify it, or may remain in a viscous form capable of maintaining a three dimensional structure. Output products are generally three dimensional structures created by a plurality of deposition layers. Fabrication software application 108 can generate tool path information for fabricator 101 and delineate how material can be used to generate shapes with entrapped air. Complex CAD programs may also be used to generate the intended geometry.

Figure 2A:
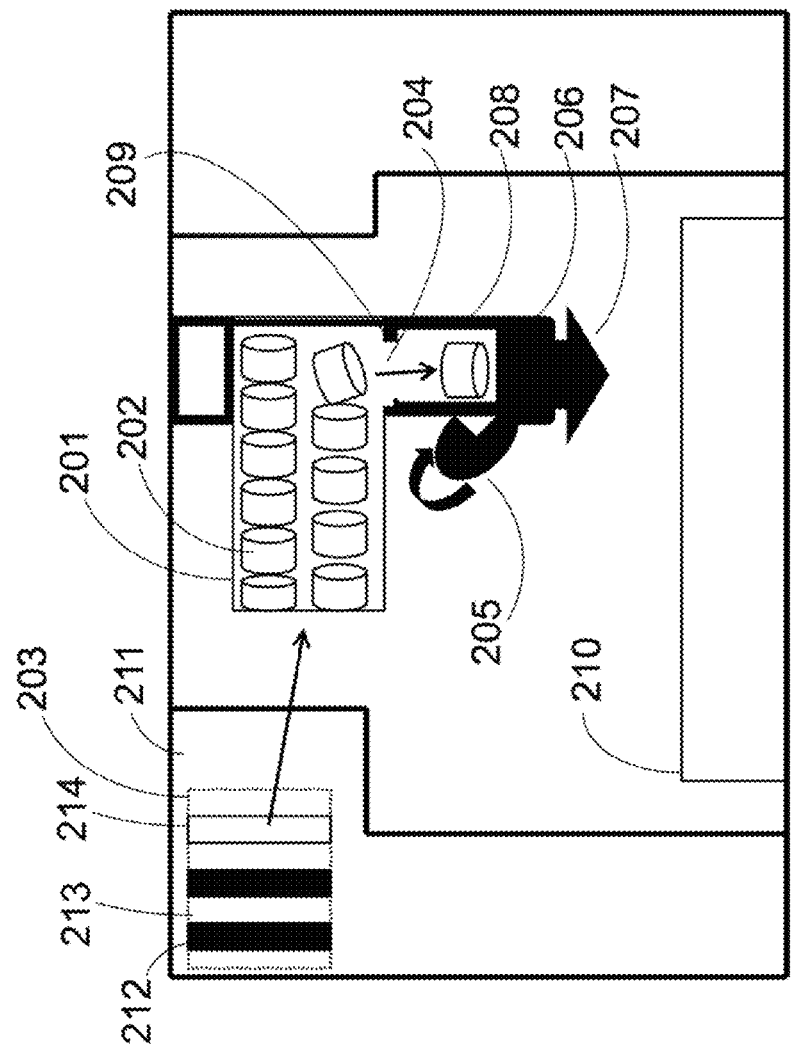
FIG. 2a is an additive manufacturing cartridge and cartridge exchange system.

Embodiments of the present invention may be implemented in any suitable three dimensional fabricating system (i.e., additive manufacturing device or 3D Printer), for example, as illustrated in FIG. 1 and described above. Other exemplary three dimensional fabricating system or components thereof are described in U.S. Pub. No. 2012/0241993 entitled "SYSTEMS AND METHODS FOR FREEFORM FABRICATION OF FOAMED STRUCTURES" and published on Sep. 27, 2012 (filed as U.S. application Ser. No. 13/356,194 on Jan. 23, 2012) and U.S. Pat. No. 7,625,198 to Lipson et. al. In one embodiment of the present invention, shown FIG. 2a, cartridge 201 comprising of several pellets of material, such as pellet 202, is loaded onto deposition head 208. Cartridge 201 opens by a door 209 to allow pellets to fall through opening 204 into deposition head 208. The pellets can be pushed through heating element 206 using motorized mechanism 205, which can push pellets into or out of heating element 206 as necessary. (Other embodiments, depending on material type and form, may or may not use a heating element, or replace/enhance it with an alternative processing step or steps.) Heating element 206 is adjoined to deposition tip (i.e., nozzle) 207 from which material is extruded onto build tray 210. Cartridges can be interchanged by moving deposition head 208 and cartridge 201 to cartridge exchange bay 203, which may be mounted on fabricator chassis 211. As can be seen in FIG. 2, cartridge exchange bay 203 may contain slots for a number of cartridges. For example, slot 212 contains another cartridge, slot 213 is unoccupied and slot 214 was previously occupied by cartridge 201, which is now coupled to deposition head 208 in the illustration. Cartridges in cartridge exchange bay 203 may be closed (i.e., disposable) or refillable.

Figure 2B:
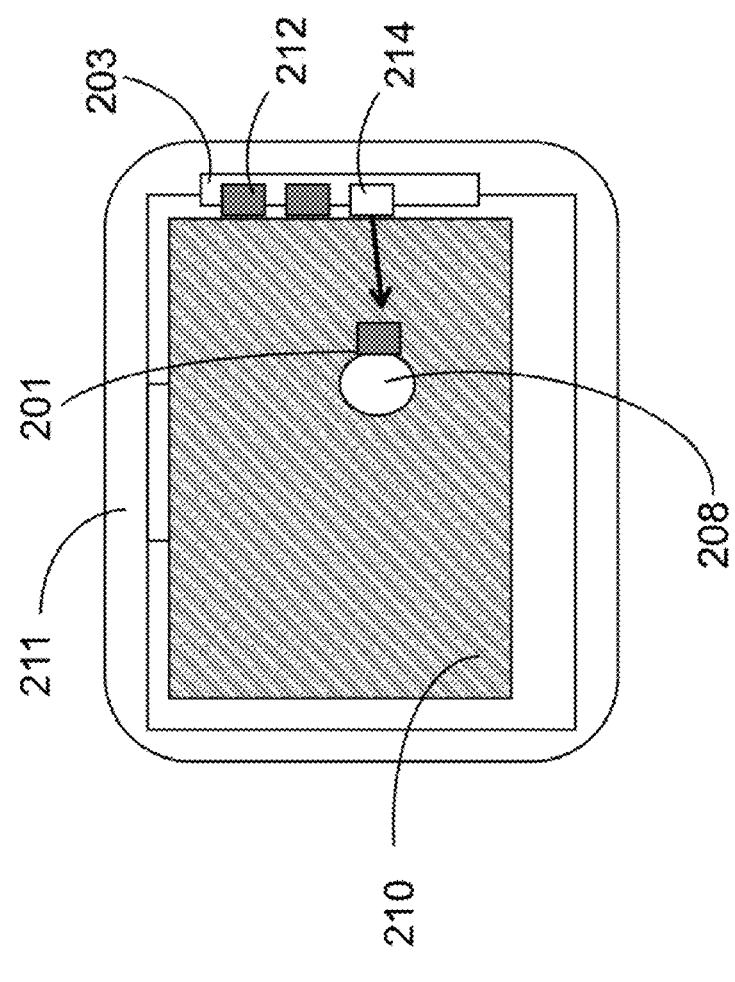
FIG. 2b depicts another angle of an additive manufacturing cartridge and cartridge exchange system.

FIG. 2b shows an embodiment with a top-down view of some components as shown in FIG. 2a. In particular, this figure shows cartridge 201 loaded onto deposition head 208. Cartridges can be interchanged by moving deposition head 208 and cartridge 201 to cartridge exchange bay 203, which may be mounted on fabricator chassis 211. Deposition head 208 may move above build tray 210 and deposit materials onto it. In exchange bay 203, slot 212 contains another cartridge and slot 214 was previously occupied by cartridge 201.

In another embodiment of the invention, all cartridges remain in cartridge exchange bay 203 mounted on fabricator chassis 211 so they will not burden deposition head 208 by increasing its weight and potentially slowing it down as it moves across build tray 210. Avoiding such increases in weight could also reduce cost to build the machine by not requiring the use of more robust components to support a heavier tool head mechanism 208. In this embodiment, deposition head 208 may return to the cartridge bay periodically to refill with additional pellets, or deposition head 208 may rely on tubing or other means to maintain a pellet feed from, e.g., cartridge 201. (Likewise, other embodiments function similarly but use fluid lines or direct filaments—as opposed to filaments created from pellets, or pellets directly without a solid-state filament intermediary—to accomplish the same.)

Figure 3:
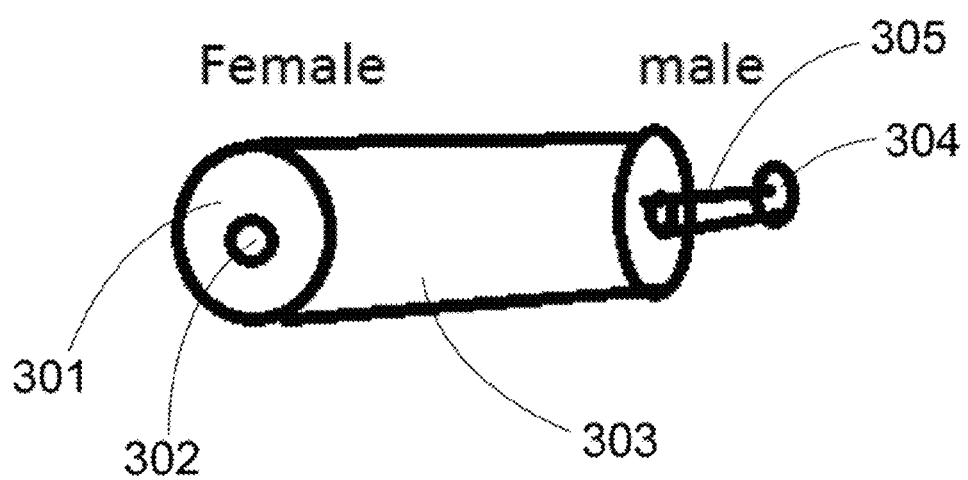
FIG. 3 is an embodiment of the pellets which may be used in this system.

The pellets may be provided in different shapes and/or sizes and numerous embodiments are possible. For example, as shown in FIG. 3, a pellet can be provided with a male and female side, such that a number of such pellets may be coupled together. Pellet 303 has female side 301 which is characterized by receiving port 302 and the male side is characterized by docking mechanism 305 and may also include locking mechanism 304 for secure connection. By snapping pellets together, several materials or several colors of the same material can be easily fused, even without heating. This allows pellets to be fused with or without the use of a cartridge system, and even manually, in order to create a multi-material and/or multi-color filament. Unlike alternative flat pellets which can be held together by forces such as gravity or pressure (also an embodiment of the present invention), a sequence of pellets like 303 can be coupled together and easily moved forward and/or backwards through a deposition head as traditional solid filaments would.

Figure 4:
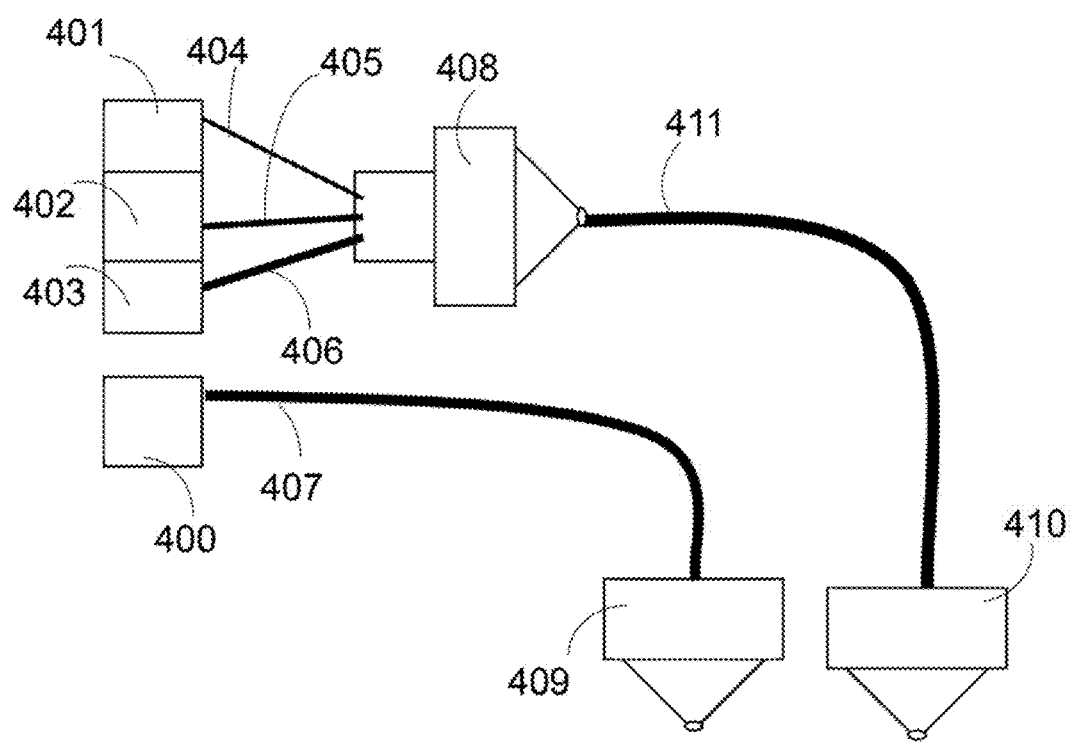
FIG. 4 is an embodiment of the invention in which the support material and the printed object material are extruded through separate nozzles.

With respect to FIG. 4, an embodiment of the present invention uses small pellets which may be made in a variety of shapes (e.g., circle, oval, square, rectangle, star-shaped, spherical, cuboid, etc). In the context of some disclosed embodiments, the diameter of each pellet may optimally be within a range of ⅛ of an inch to 1½ inches, although pellets with a diameter bigger or smaller than this exemplary range may also be used. The illustration depicts this system used in a plastic output product manufacturing scenario. Material feeder lines 404, 405 and 406 could be replaced with fluid lines for use in a similar manner with a viscous material, whether in pellet or fluid form within cartridges 401, 402 and/or 403, and some embodiments may need to be directed through heating and/or extrusion head 408 before ultimate deposition through deposition tip 409 or 410. (It should be understood that any difference in thickness between lines 404, 405, 406, 407 and 411 as shown in FIG. 4 is for illustration purposes only, the feed lines of the embodiment may be of equal or different thickness.) Shown on the left are cartridge bays 400, 401, 402 and 403 which may have several cartridges loaded, including several colors of a single material (or distinct, but combinable materials) which may take the form of filaments, viscous fluids or pellets which are gated mechanically and roll down material feeder lines 404, 405, 406 and an alternate material feeder line 407. Such a gating system assures the correct material is released from the cartridge in order to properly execute subsequent steps in the fabrication process, including appropriate mixing, fusing, or heating. The varying colors and/or materials are denoted by different types of dashed lines 404, 405, 406 and 407. The system here uses multi-tip deposition head comprising 409 and 410 because the materials being deposited may not all be fused effectively prior to deposition. For example, cartridge bay 400 may provide "support" material to feeder line 407 which may be dissolved or otherwise removed. Pellets from cartridge bays 401, 402 and 403 may be released into first stationary heating (or else processing) and/or extrusion head 408 where they are formed into multi-color (or multi-material, or multi-color and multi-material) filament 411 which is fed into the deposition tool head that deposits onto a build surface. In situations where the volume of material needed is not evenly divisible by the volume of the pellets, the deposition head may deposit excess material in a different location on the build surface that is distinct from the output product. Pellets from cartridge bays 401, 402 and 403 may comprise different materials, so long as they are compatible and can be attached sequentially or mixed for deposition onto a build surface for an output product. Other embodiments may have a combination of fusing, mixing, reactive steps to occur at the first extrusion head 408, which may more generally be referred to as a material chamber for processing the material as described herein.

Figure 5:
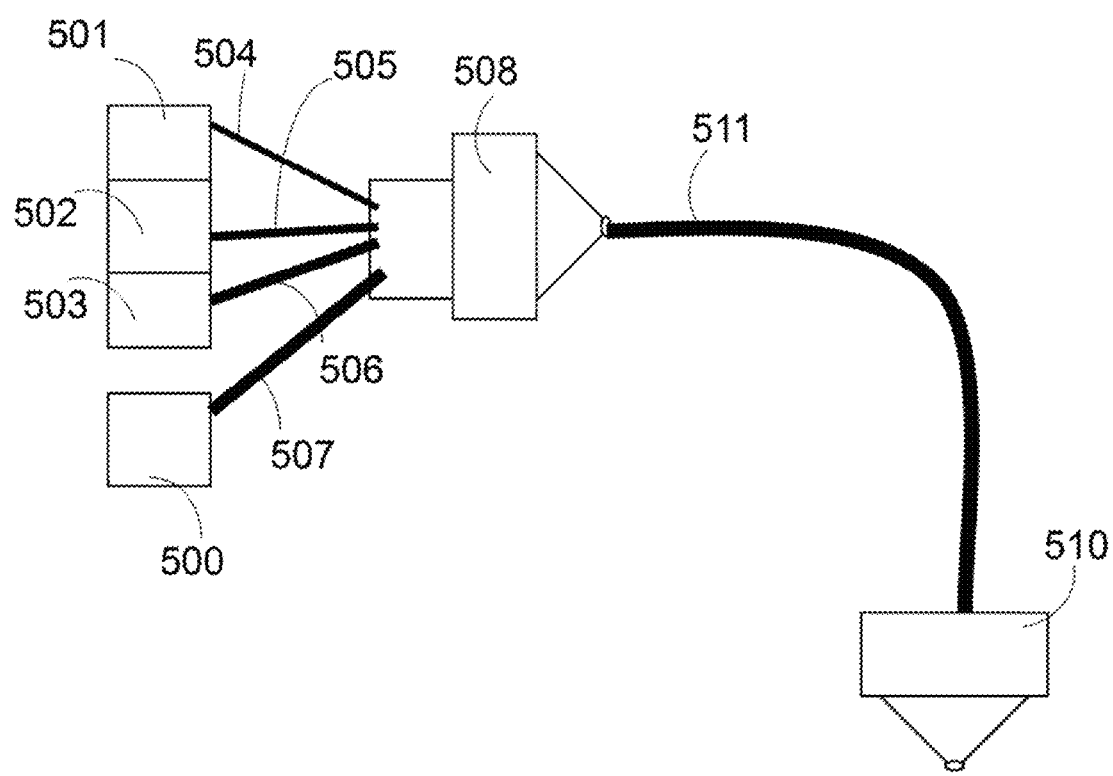
FIG. 5 is an embodiment of the invention in which the support material and the printed object material are extruded a single nozzle.

In another embodiment of the present invention, illustrated in FIG. 5, all material pellets can be fused into a single filament. As noted previously, pellets can be replaced with filaments or viscous materials that are released from, e.g., cartridges 500, 501, 502, and 503 as appropriate, which may or may not require an environmental change like heating, and may be extruded into a "filament" 511 which may be a viscous fluid. The materials may be several colors of the same material, or different materials entirely, such as support materials. The materials, such as pellets, solid-state filaments, or fluids, are fed from cartridges 500, 501, 502 and 503 as either filaments or fluids to material feeder lines 504, 505, 506 and 507 to first extrusion head 508 for fusing, and combined into a final multi-material and/or multi-color filament or fluid line when required. (It should be understood that any difference in thickness between lines 504, 505, 506, 507 and 511 as shown in FIG. 5 is for illustration purposes only, the feed lines of the embodiment may be of equal or different thickness.) Segmented regions of separate materials and/or colors may be produced, as well as hybrid regions of combination colors and/or materials mixed in first extrusion head 508, as directed by software operating the device. Per instructions in, or provided to, the software, colors and/or materials can be mixed to form new colors and/or materials. First extrusion head 508 may output material to line 511 to be deposited by tip deposition head 510 such that the final printed object resulting from deposition 510 is created with different colors and/or materials present as specified by the software.

Figure 6:
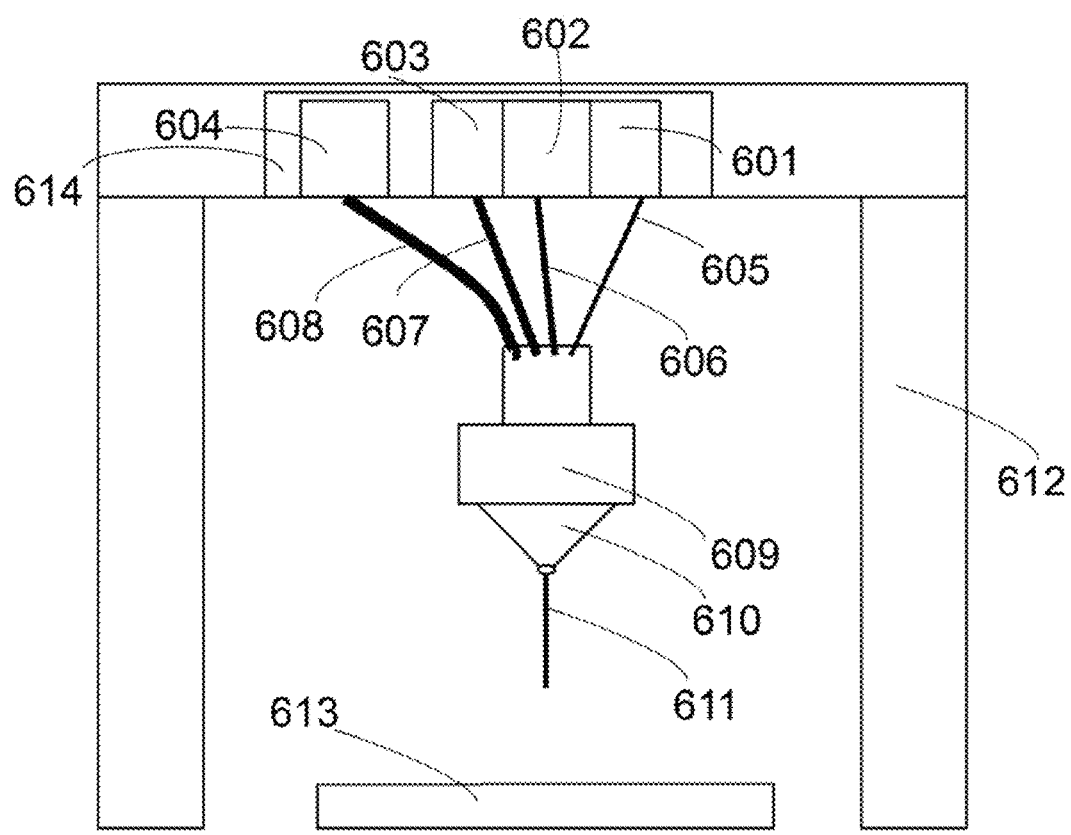
FIG. 6 is another embodiment of the invention in which the cartridge bay is located above a single deposition head and is not supported by the same mechanism as the deposition head, and is supported by the device mainframe.

In an embodiment of the present invention shown in FIG. 6, cartridge bay 614 and cartridges 601, 602, 603 and 604 are located above single deposition head 609. Unlike other described embodiments of the present invention where a cartridge is mounted onto the same movable mechanism as the deposition tool head comprising 609, 610, which deposits material 611 onto build tray 613, in FIG. 6 it is shown that cartridge bay 614 may alternatively be supported by device chassis 612 and provide material feed lines 605, 606, 607 and 608 to movable deposition tool head comprising 609 and 610. It should be understood that any difference in thickness between lines 605, 606, 607 and 608 as shown in FIG. 6 is for illustration purposes only, the feed lines of the embodiment may be of equal or different thickness.)

In the embodiment of FIG. 6, component 609 may be a single heating element or 609 may be two heating elements stacked on top of one another, with space to cool a short filament in order to help push the filament forward and/or backwards through extrusion head 610, as is sometimes needed in embodiments of the present invention in which the materials are plastics. Material feed lines 605, 606, 607 and 608 may be tubes for pellet balls to pass through, and movable deposition head comprising 609 and 610 may deposit filament material 611 onto build tray 613. Alternatively, instead of pellets being used in cartridges 601-604, material feed lines 605-608 may contain filaments, or may be fluid lines to support fluid material deposition.

Figure 7:
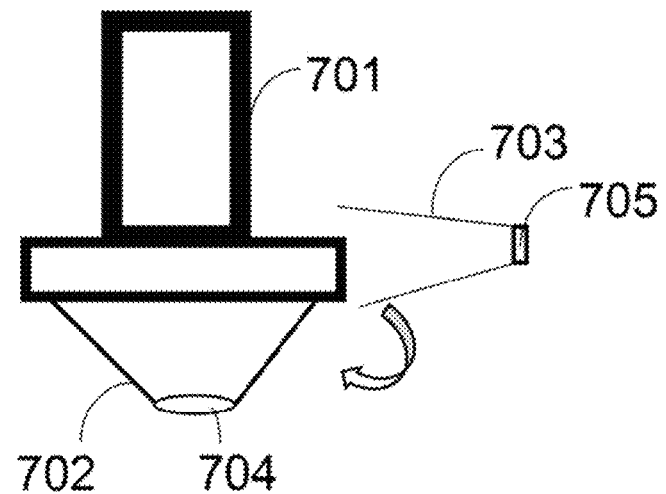
FIG. 7 is a mechanism of interchanging built-in tips, and to examples of differently shaped lumen.

To adjust the width or shape of a deposition opening, deposition tips may be interchanged with a manual or automatic mechanism. As shown in the embodiment depicted in FIG. 7, deposition head 701 may interchange large tip 702 with elliptical opening 704 for another tip, such as smaller tip 703 with rectangular 705 opening. A variety of other shapes and sizes may be interchanged, as appropriate, to allow the manufacturing device to most accurately manufacture an output product with minimal "resolution" zigzags. The process can be optimized for speed or resolution depending on default settings or user input, and the manufacturing device can be directed to appropriately interchange deposition tips as necessary, without individual instructions.

Figure 8:
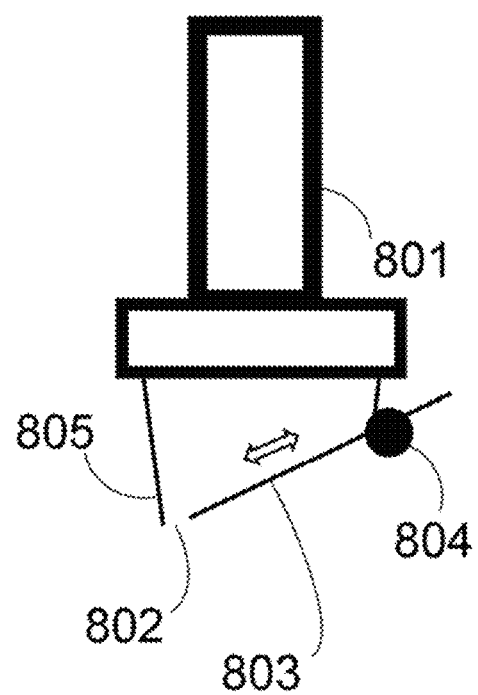
FIG. 8 is an embodiment of the invention in which the lumen of the built-in tip is changed in size and/or shape mechanically.

In another embodiment of the invention, as depicted in FIG. 8, deposition head 801 may have a single manually or mechanically adjustable deposition tip comprising of modifiable or flexibly-shaped and sized opening 802, which, for example, may be adjusted by movable component 803 which is controlled by mechanical device 804, in conjunction with non-movable component 805. It should be appreciated that there are other similar mechanisms for manually or mechanically (or otherwise, i.e., electronically, magnetically, etc.) adjusting a deposition tip to change the shape and size of its output. For example, component 805 can also be moveable and controlled by a mechanical device similar to that of mechanical device 804.

In an alternative embodiment of the present invention, movable component 803 may be perforated with a plurality of openings, each with different shapes and/or sizes, and may interact with stationary component 805 to provide a particular shape and size opening for the deposition tool head at a given time. Alternative embodiments of the present invention may rely on other means to change the shape and size of the deposition tip, such as via electromagnetic force.

Figure 9:
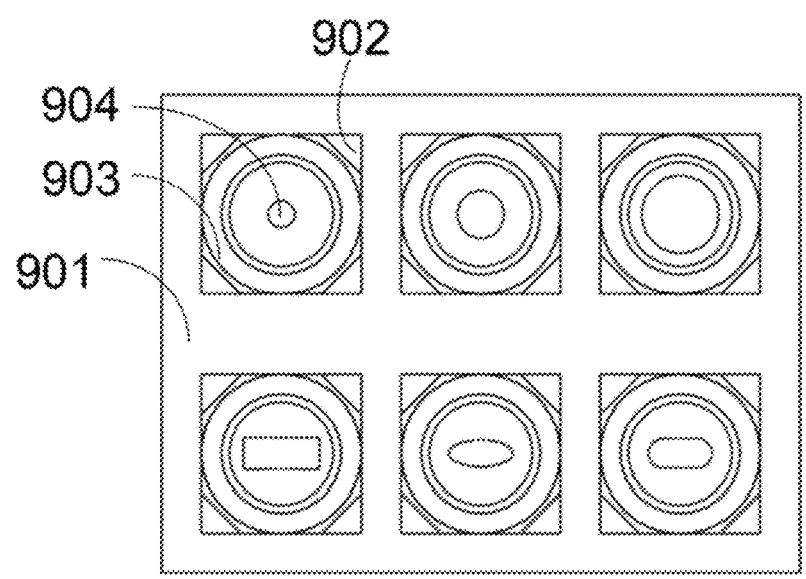
FIG. 9 is an embodiment of the invention in which the tips of varying lumen shapes and/or sizes are held in a container separate from tool head.
Figure 10:
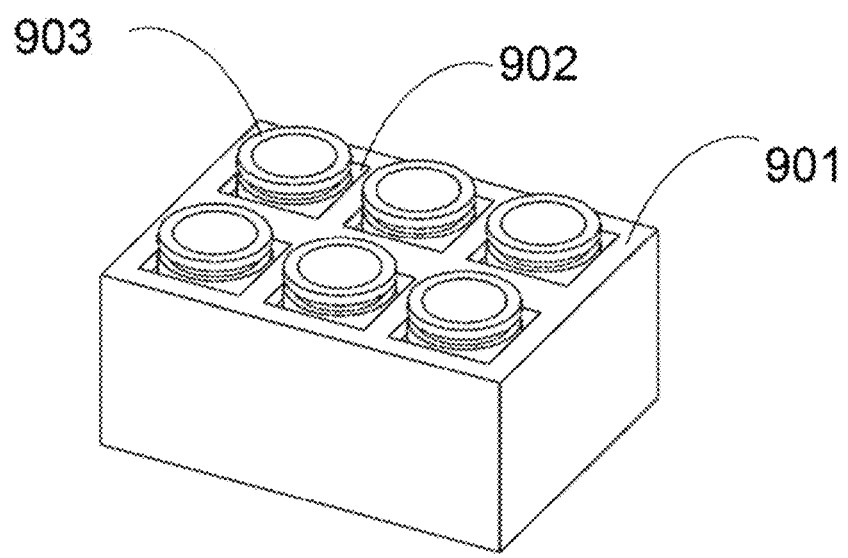
FIG. 10 depicts another angle of the embodiment shown in FIG. 9 in which the tips of varying lumen shape/size are held in a container separate from tool head.
Figure 11:
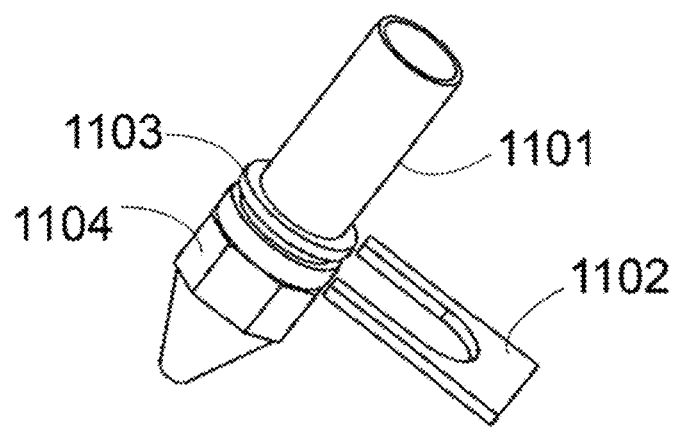
FIG. 11 in an embodiment of a locking mechanism for tip exchange in this invention, with the locking mechanism detached.
Figure 12:
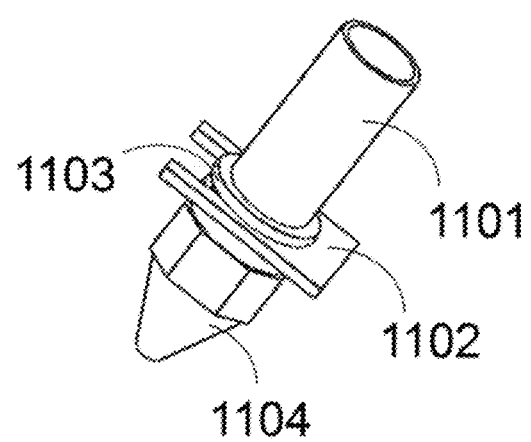
FIG. 12 depicts another angle of an embodiment of the locking mechanism for tip exchange in this invention, with the locking mechanism engaged.
Figure 13:
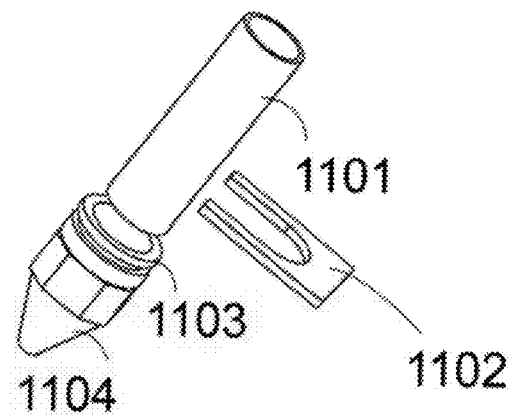
FIG. 13 depicts another angle of an embodiment of the locking mechanism for exchange this invention, with the locking mechanism and tip detached.
Figure 14:
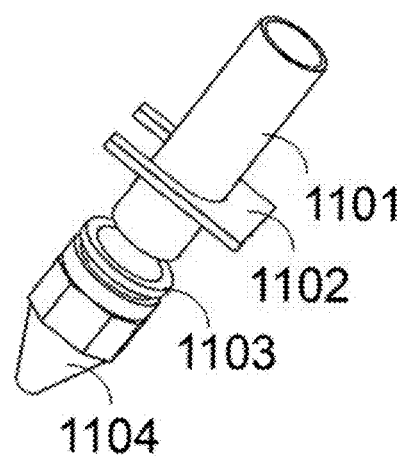
FIG. 14 depicts another angle of an embodiment of the locking mechanism for tip exchange in this invention.

To adjust the width or shape of the deposition opening deposition tips may be interchanged dynamically (e.g., manually or mechanically) by a device on the fabricator or the deposition tool head itself. As shown in an embodiment of the present invention depicted in FIGS. 9 and 10, a fabricator may return deposition tip 903 from a deposition tool head to compartment 902 in tip dispenser box 901, which is comprised of several compartments, each capable of storing a deposition tip. As with deposition opening 904 in deposition tip 903, each deposition tip in dispenser box 901 may have a deposition opening with a particular shape and size that can be selected for use by the deposition tool head. Deposition tips such as 903 may be heated while not in use (i.e., while in dispenser box 901) in order to allow for smoother changing between tips, in other words, so the deposition tool head will not be cooled as a result of changing tips. Deposition tips in dispenser box 901 may also be heated above or below the standard deposition temperature in order to help create or break a seal. Likewise, deposition tips and deposition tool heads may be made of materials with heat absorption properties that differ in order to help create seals, as well. Finally, other environmental controls may also be used in a similar manner to the heating described above. This could include temperature or pressure controls, as well as other appropriate controls, such as placement into to liquid bath for sterilization, or lubrication, etc.

As noted above, deposition tips may be interchanged dynamically (e.g., manually or mechanically) to adjust the width or shape of a deposition opening. As shown in an embodiment of the present invention illustrated in FIGS. 11, 12, 13 and 14, deposition tool head shaft 1101 can connect with interchangeable tip 1104 and be secured in place by locking mechanism 1102, which attaches to locking junction 1103.

Figure 15:
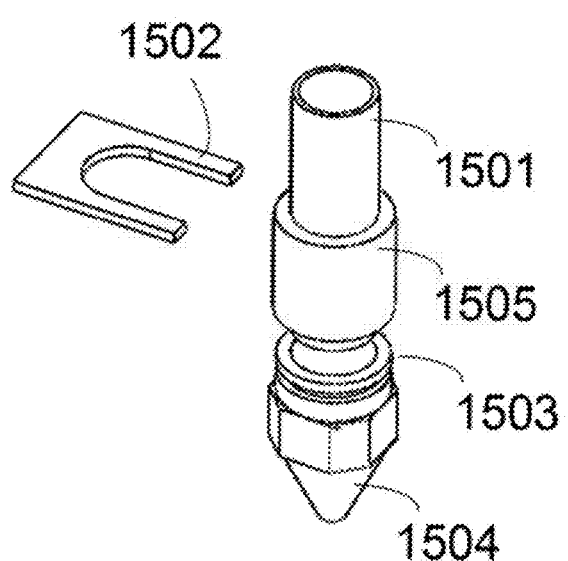
FIG. 15 is an angle of an embodiment of the locking mechanism for tip exchange in this invention, with an ejection mechanism for removing a tip.

As shown in an embodiment of the present invention as depicted in FIG. 15, tool head shaft 1501 can connect with interchangeable tip 1504 and be secured in place by locking mechanism 1502 which attaches to locking junction 1503. Ejection mechanism 1505 can be used to release a tip from tool head shaft 1501. Many similar mechanisms can be used to help the machine manually or mechanically interchange tips. For example, an embodiment of the present invention can use a magnetic interchange system, an electromagnetic system, a latching mechanism, or an automatic rotor screw mechanism.

Figure 16:
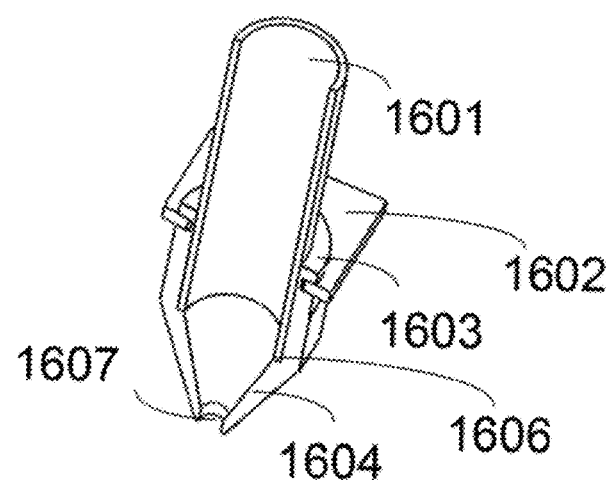
FIG. 16 is a cross section of a tip exchange mechanism.
Figure 17:
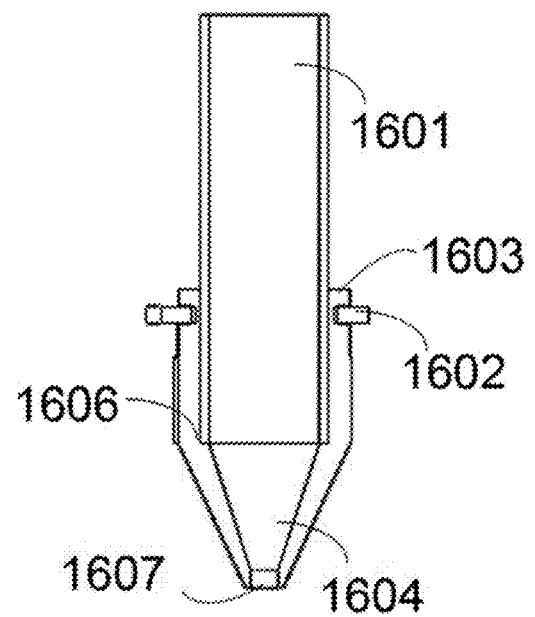
FIG. 17 is another cross section of the tip exchange mechanism shown in FIG. 16.

As shown in an embodiment of the present invention depicted in FIGS. 16 and 17, tool head shaft 1601 can connect with interchangeable tip 1604 and be secured in place by locking mechanism 1602 which attaches to locking junction 1603. Junction 1606 between tip 1604 and tool head shaft 1601 can form a tight seal that allows material to flow through tool head shaft 1601, interchangeable tip 1604 and out through lumen 1607.

Figure 18:
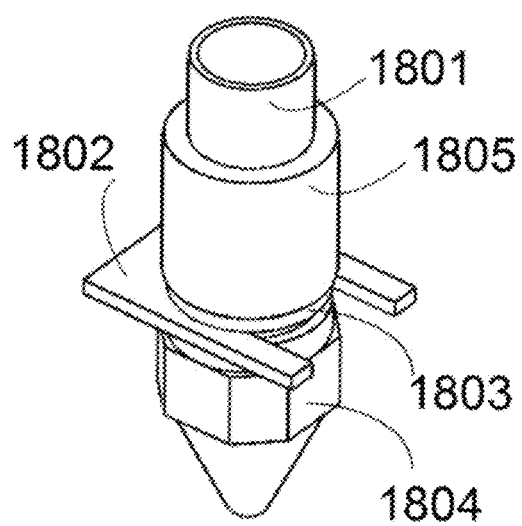
FIG. 18 depicts is an angle of an embodiment of the locking/ejection mechanism for tip exchange in this invention.

As shown in an embodiment of the present invention depicted in FIG. 18, tool head shaft 1801 can connect with interchangeable tip 1804 and be secured in place by locking mechanism 1802 which attaches to locking junction 1803. Ejection mechanism 1805 can be used to release interchangeable tip 1804 from tool head shaft 1801.

The described pellet based cartridge system for additive manufacturing has several distinct advantages over current systems including the ability to use a smaller, lighter tool head because the weight of the on-board material can be minimal, so it can divert weight from the tool head to the stationary cartridge area heating mechanism. The system also allows deposition tool heads to be stowed in the machine while another tool head (e.g., a milling tool) is interchanged on the same machine. In this fashion, a deposition tool head can maintain an unbroken filament (should it be preferred in the embodiment) from the cartridge-side heating chamber to the tool head, even when that tool head is not mounted and/or another deposition tool head is being used. In an embodiment of the present invention supporting the pellet based system, materials can be mixed (with a mechanical mechanism, turbulence, or convection) to allow a customized material to be generated. With respect to embodiments of the present invention, materials may be comprised of, e.g., plastics, silicones, rubbers, gels, resins, food items, biological or organic substances, etc. For example, two or more colors of plastic can be released into the cartridge-side heating chamber to yield a new color, allowing a basic set of colored plastics to yield plastic output products with colors from the entire color spectrum. Although this example uses heating of plastic to effect environmental change in the material, other environmental changes in conjunction with a range of materials can be used in, e.g., the tool head or mixing chamber, such as changes in pressure, UV light, etc.

Figure 19:
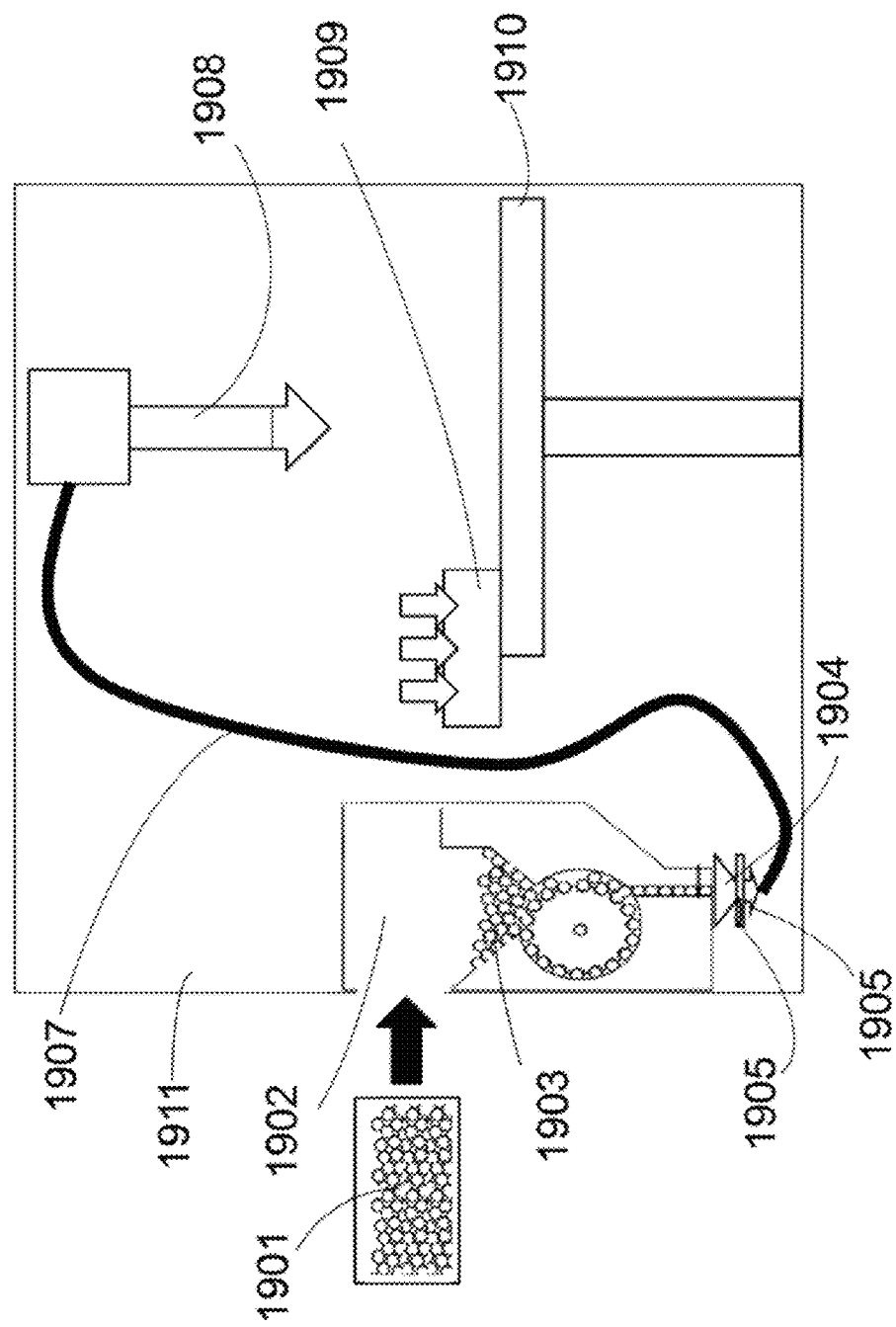
FIG. 19 is an embodiment of the pellet based cartridge system with interchangeable tip box.

The embodiment of the invention shown in FIG. 19 shows additive manufacturing apparatus 1911 with cartridge based deposition tool head 1908 attached. The embodiment can be used when cartridge 1901 is inserted into one of several cartridge bays 1902, which allow the beads or pellets to collect in hopper catch 1903. From there, the pellets may descend into multi-material catch 1904, heating chamber 1905, and stationary extrusion head 1906. The material can then be extruded into filament 1907, which is leads (e.g., possibly via tube) to manufacturing deposition tool head 1908. Also shown is build platform 1910 and tip box 1909, which may enable deposition head 8 to interchange tips.

Figure 20:
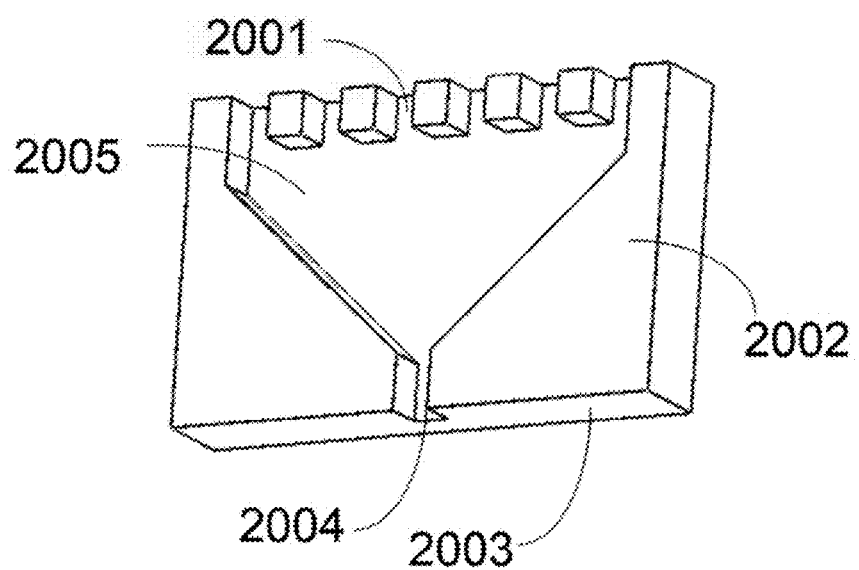
FIG. 20 is the multi-material/multi-color catch for collection of pellets from cartridges, which may lead to a heating or other processing chamber, if appropriate to the material.

FIG. 20 shows an embodiment of multi-material catch 2002, into which pellets from several cartridges can be collected prior to heating and/or processing. Several openings such as 2001 can allow material from different cartridges to enter collecting area 2005. The bottom end of multi-material catch 2003 can be set to face a heating element (or other processing unit) adjacent to it. The pellets can descend through distal opening 2004.

Figure 21:
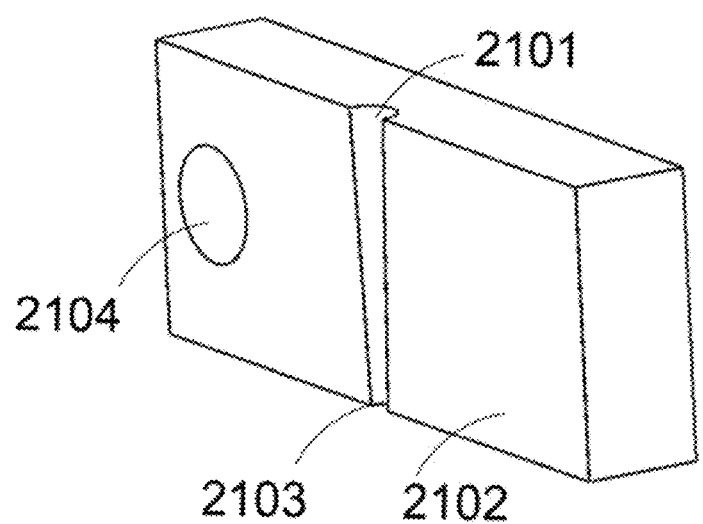
FIG. 21 is an embodiment of the heating/mixing element.

In the embodiment shown in FIG. 21, there is a heating element 2102 and heat source 2104, proximal entry 2101, as well as distal exit 2103, which can interface with a deposition tip mechanism.

Figure 22:
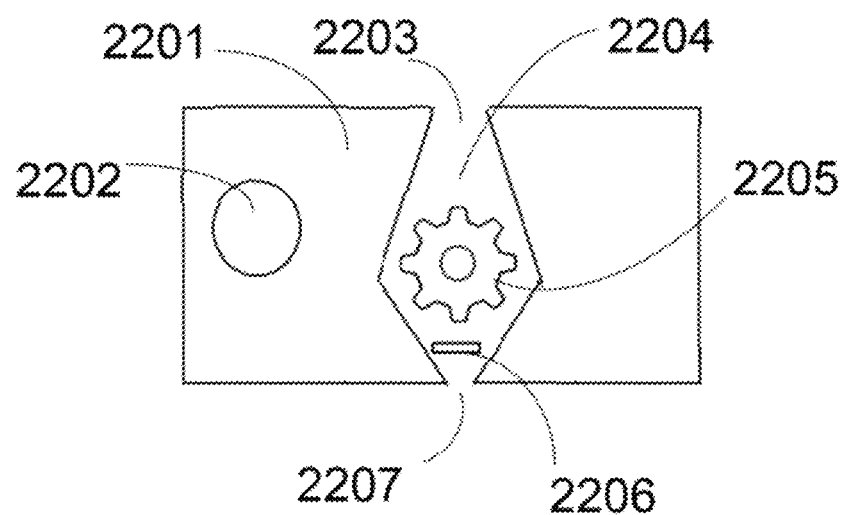
FIG. 22 is another embodiment of the heating/mixing element.

In the embodiment shown in FIG. 22, there is a heating element 2201 and heat source 2202. Pellets enter through the proximal entry 2203 and can mix and melt in heating chamber 2204. To assist in the mixing process, mechanical device 2205 and additionally, or alternatively, turbulence inducing protrusion 2206 may also be used. Distal exit 2207 can be adjacent to a deposition tip mechanism.

Figure 23:
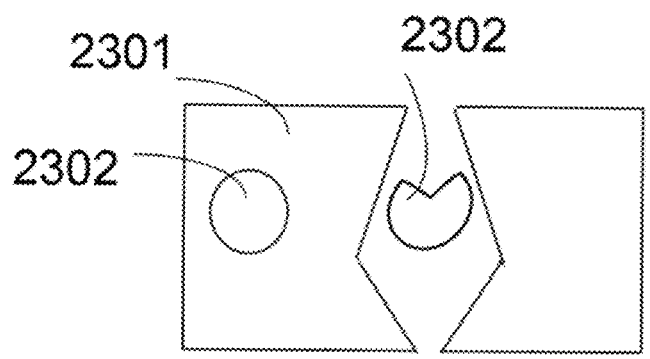
FIG. 23 is another embodiment of the heating/mixing element.

In the embodiment shown in FIG. 23, there is a heating element 2301 and heat source 2304, with an optional turbulence causing mechanism 2302 that can assist with mixing and heating material.

Figure 24:
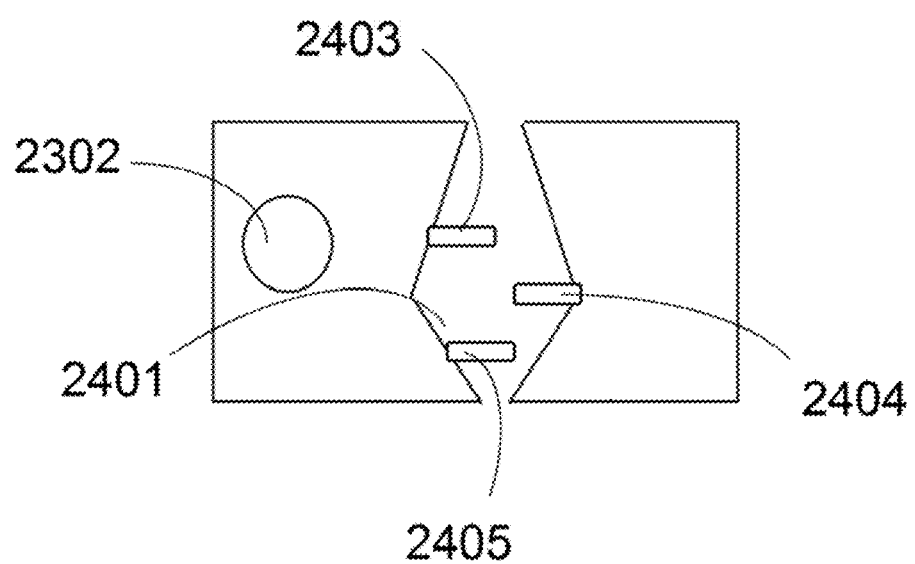
FIG. 24 is another embodiment of the heating/mixing element.

In the embodiment shown in FIG. 24, there is a heating element chamber 2401 and heat source 2402, with optional turbulence causing mechanisms 2402, 2403, 2404 to assist with mixing and heating material.

Figure 25:
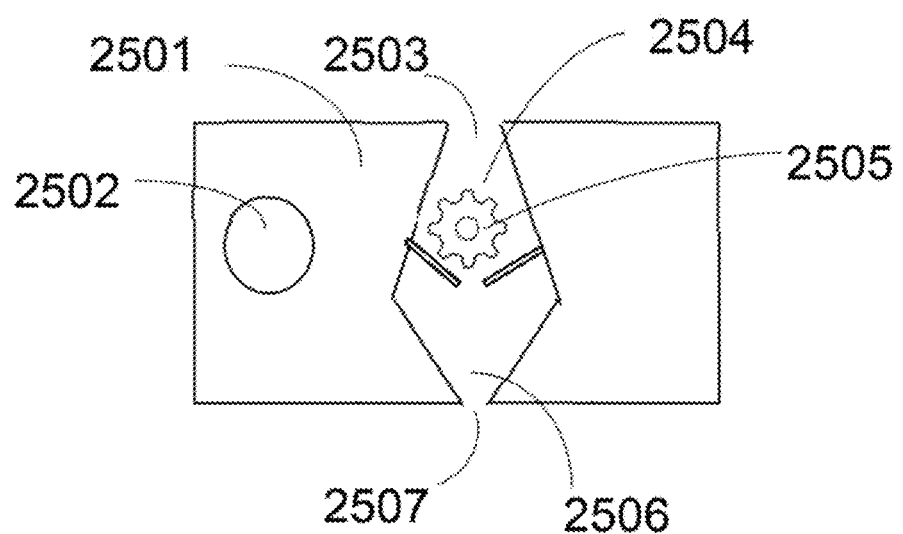
FIG. 25 is another embodiment of the heating/mixing element.

In the embodiment shown in FIG. 25, there is a heating element 2501, heat source 2502, and proximal opening 2503, which leads into mixing chamber 2504. Mixing chamber 2504 has mechanical mixing and/or turbulence mixing mechanism 2505, which may be enabled to assist in the mixing of material. Mixing mechanism 2504 may therefore actively mix material, or not active and simply allow materials to pass through it if preferred, for example, if there is a lot of just one material type passing through. Distal chamber 2506 feeds into distal exit 2507, which may lead to a deposition apparatus.

Figure 26:
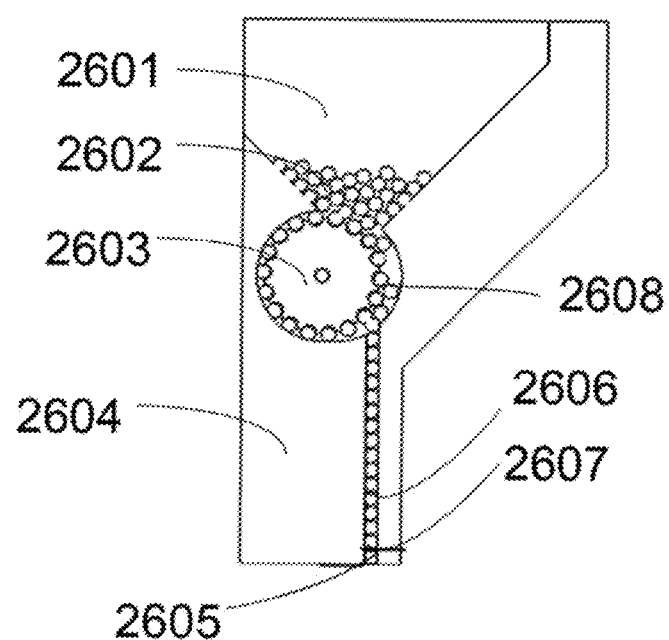
FIG. 26 is an embodiment of the invention which uses a hopper catch to interface with the pellet cartridges.

In the embodiment shown in FIG. 26, mechanism 2604 may be used as part of a cartridge system. Hopper catch 2601 holds pellets 2602 which are loaded in from a cartridge and fall (or pushed) into continuous rotation apparatus 2603, which may be used to prevent jamming by circulating pellets around a loop, with one or two pellets worth of space 2608 being suggested. This technique can smoothly guide pellets down into proximal tunnel 2606 and out distal tunnel opening 2605 when door 2607 is open, and prevents pellets from getting stuck or jammed due to the motion of repeated opening and closing of door 2607 or other motion occurring within mechanism 2604.

Figure 27:
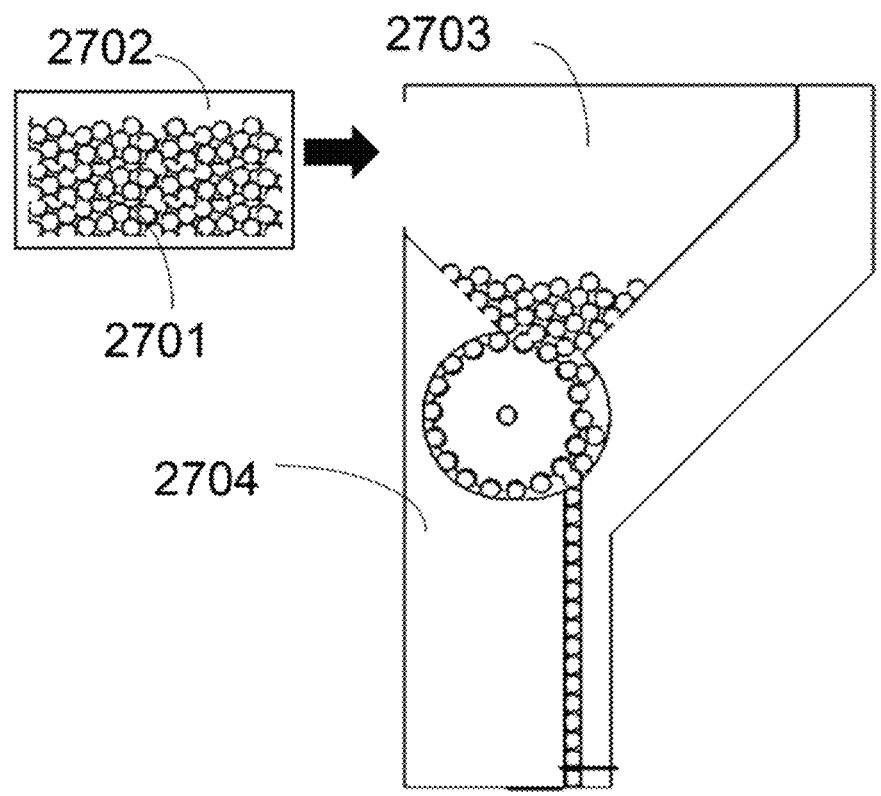
FIG. 27 is an embodiment of the invention which uses a hopper catch to interface with the pellet cartridges, depicting both the catch and cartridge.

In the embodiment shown in FIG. 27, cartridge 2702 contains pellets 2701 and can be inserted into opening 2703 to stationary hopper mechanism 2704.

Figure 28:
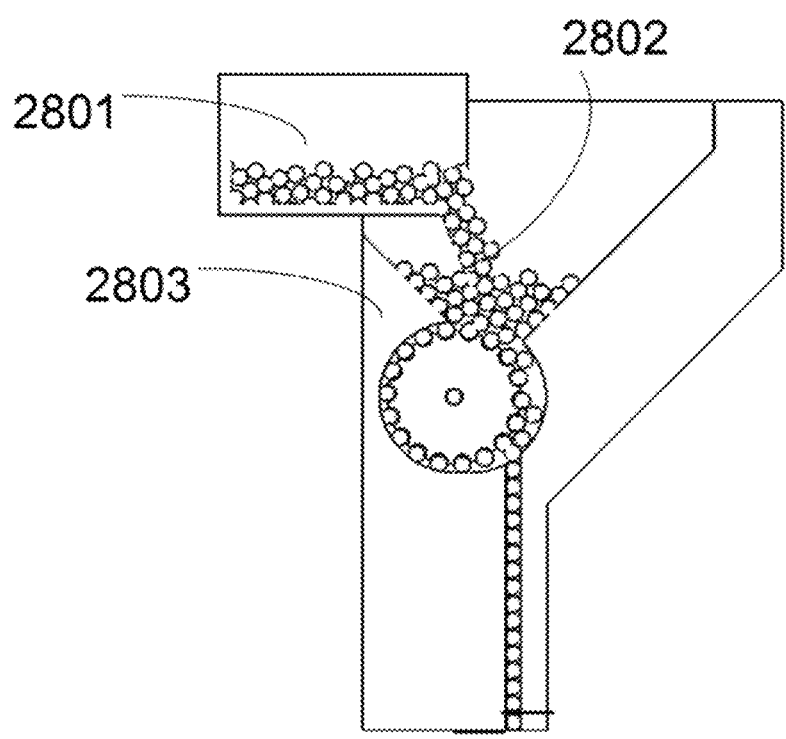
FIG. 28 is an embodiment of the invention which uses a hopper catch to interface with the pellet cartridges, depicting pellets pouring from the cartridge into the catch.

In the embodiment shown in FIG. 28, hopper mechanism 2803 has cartridge 2801 inserted into it with pellets 2802 pouring into the catch.

Figure 29:
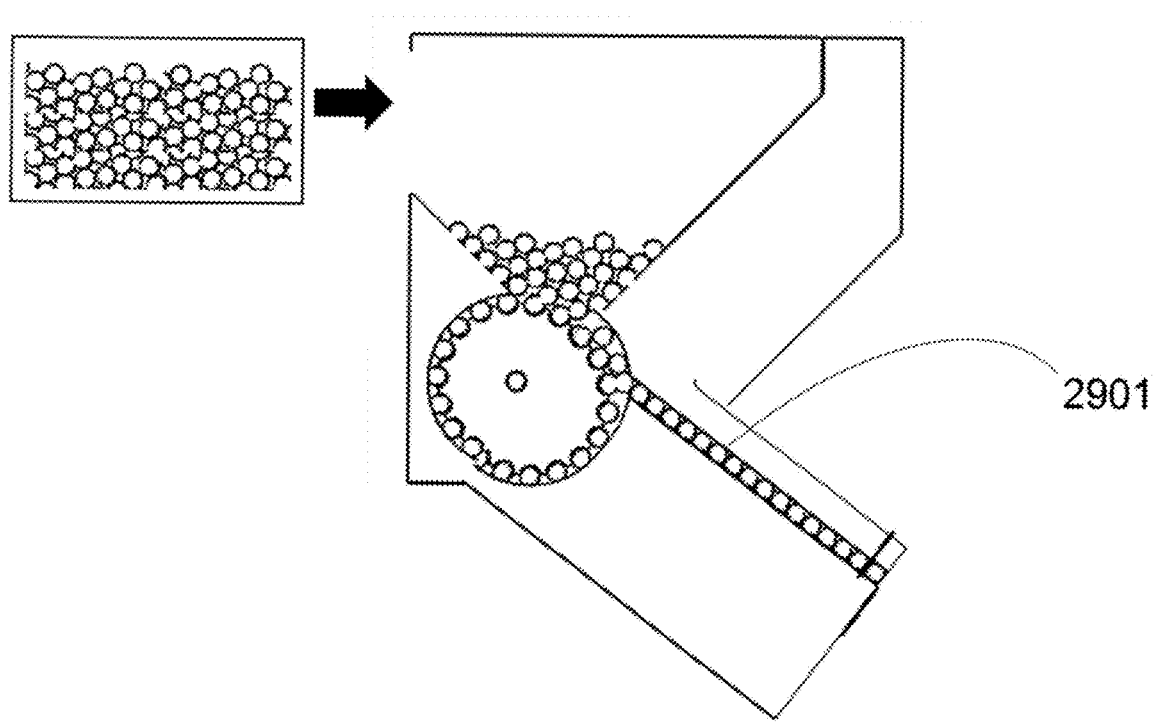
FIG. 29 is another embodiment of the invention, with the hopper catch oriented differently.

In the embodiment shown in FIG. 29, distal tunnel 2901 is at a different angle than has been previously shown in one or more other figures herein.

Figure 30:
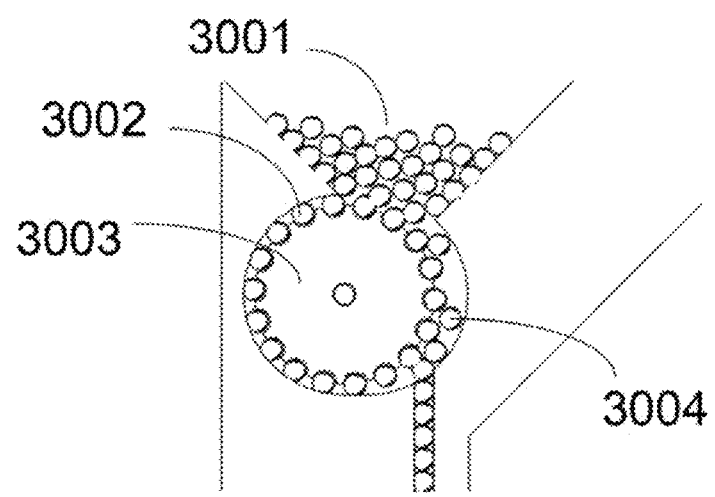
FIG. 30 is a detailed view of the continuous rotation system which the hopper guides the pellets.

In the embodiment shown in FIG. 30, another illustration is provided for a continuous rotation system 3003 that guides pellets 3002 from catch 3001 around loop 3004.

Figure 31:
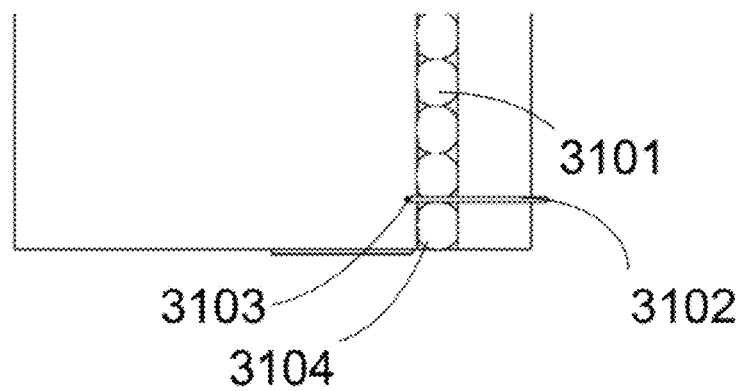
FIG. 31 is a pellet exiting from the hopper, and others being trapped behind the door.

In the embodiment shown in FIG. 31, another illustration is provided for a tube beneath a continuously rotating mechanism. Pellets may be held in proximal portion of a tube above door 3102 (such as Pellet 3101). This figure shows door 3102 having been moved into closed position 3103, after allowing pellet 3104 to pass through it. The proximal portion of the tube portion above door 3102 may be used as a buffer.

Figure 32:
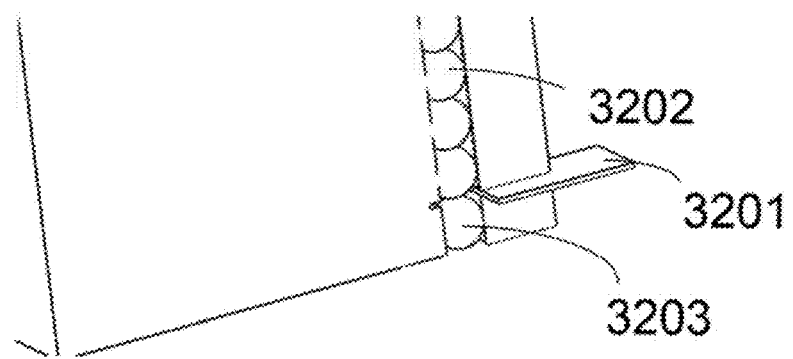
FIG. 32 is the trap door of the hopper opened, allowing pellets to flow.

In the embodiment shown in FIG. 32, another illustration is provided for a tube beneath a continuously rotating mechanism. Pellets (such as Pellet 3202) may be held in a proximal portion of the tube above door 3201 that is contiguous with the hopper. In this illustration, door 3201 is in an open position, allowing Pellet 3203 to pass through and be directed toward, e.g., a stationary extrusion tip (or in the case where only a single extrusion mechanism is present, the moving, manufacturing extrusion tip).

Figure 33:
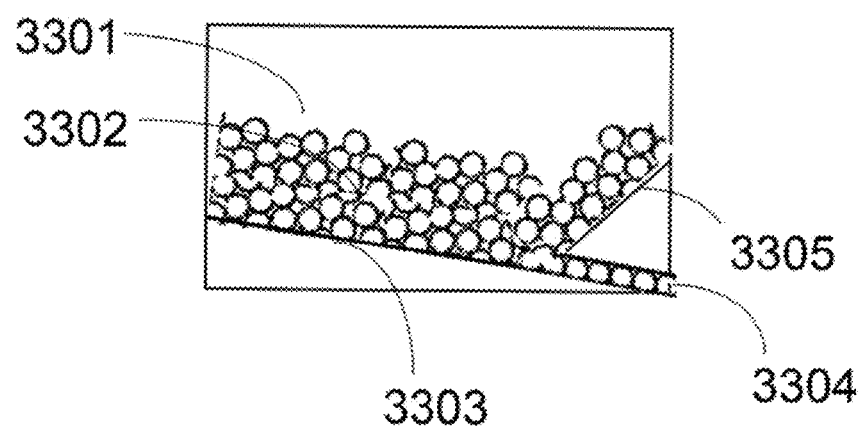
FIG. 33 is an embodiment of a cartridge which can be used with this system.

In the embodiment shown in FIG. 33, an illustrated cartridge system may be used with or without a hopper mechanism. Cartridge 3301 containing pellets 1302, which may or may not be spherical (the pellets are not shown to scale). Pellets 3302 may be channeled through opening 3304 by rolling down primary ramp 3303 or secondary ramp 3305. A cartridge may be removable (either disposable or refillable) and can optionally have a pin in it to allow insertion of a continuous rotation alignment and/or anti-jamming mechanism.

Embodiments of the cartridge system described herein can allow multiple materials to be fused (e.g., diffused, mixed, or stacked) to form a filament. Filament formed in the additive manufacturing device itself (as opposed to in advance) can then be deposited. The filament may be constructed to accommodate a particular mix of materials and/or colors desired for fabricating a product or object. An object is envisioned as sliced into layers, deposition paths can then be identified, and a filament with an appropriate mix of materials and/or colors can be created by the device. For example, if the first layer of an object needs pink plastic and support, the first segments of the filament might be comprised of pink plastic and a support material, having originated from cartridges containing red plastic, white plastic (e.g., ABS), and a dissolvable plastic support material. (Support materials may be easily separated from an output product after a job is complete and may thereby allow for complex geometries that would be otherwise impossible or impractical.

An alternative embodiment of the present invention involves using a single color of a single material, e.g., white plastic. Cartridges of dyes could then be added to a heating chamber to be mixed. This could be implemented systems which have one or two deposition heating chambers. The system would resemble those examples illustrated herein; however, dyes could be added and a dyed filament calculated and created as described. Reactants may likewise also be added to cause chemical reactions, should one wish to alter the material(s) Cartridges in embodiments of the present invention may also be spring loaded, magazine fed, or depressed. Materials may or may not require a heating chamber, and may or may not react chemically.

Deposition tips may be interchanged such that a thin tip might be used to deposit a fine path around the outer border of a layer, while a thicker tip can allow more material to flow out in a given amount of time and be used for solid inner parts of a layer in order to speed up the deposition process.

Embodiments of the present invention may also be used to fabricate food items which might be fried in deep fryer. In such a case, a fat-like material, such as shortening could be used as a support material, which would dissolve away upon frying. This could allow for creation of unique geometries that would otherwise be impossible or impractical.

Embodiments of the present invention can be used in a manner in which the processing of data required to operate the device occurs on a computing device which is not directly attached and may or may not be fully accessible to the user, such as a remote server. Such a server may operate one or more devices simultaneously.

Embodiments of the present invention can be used with disposable deposition tips, and the device may have a designated disposal area.

Figure 34:
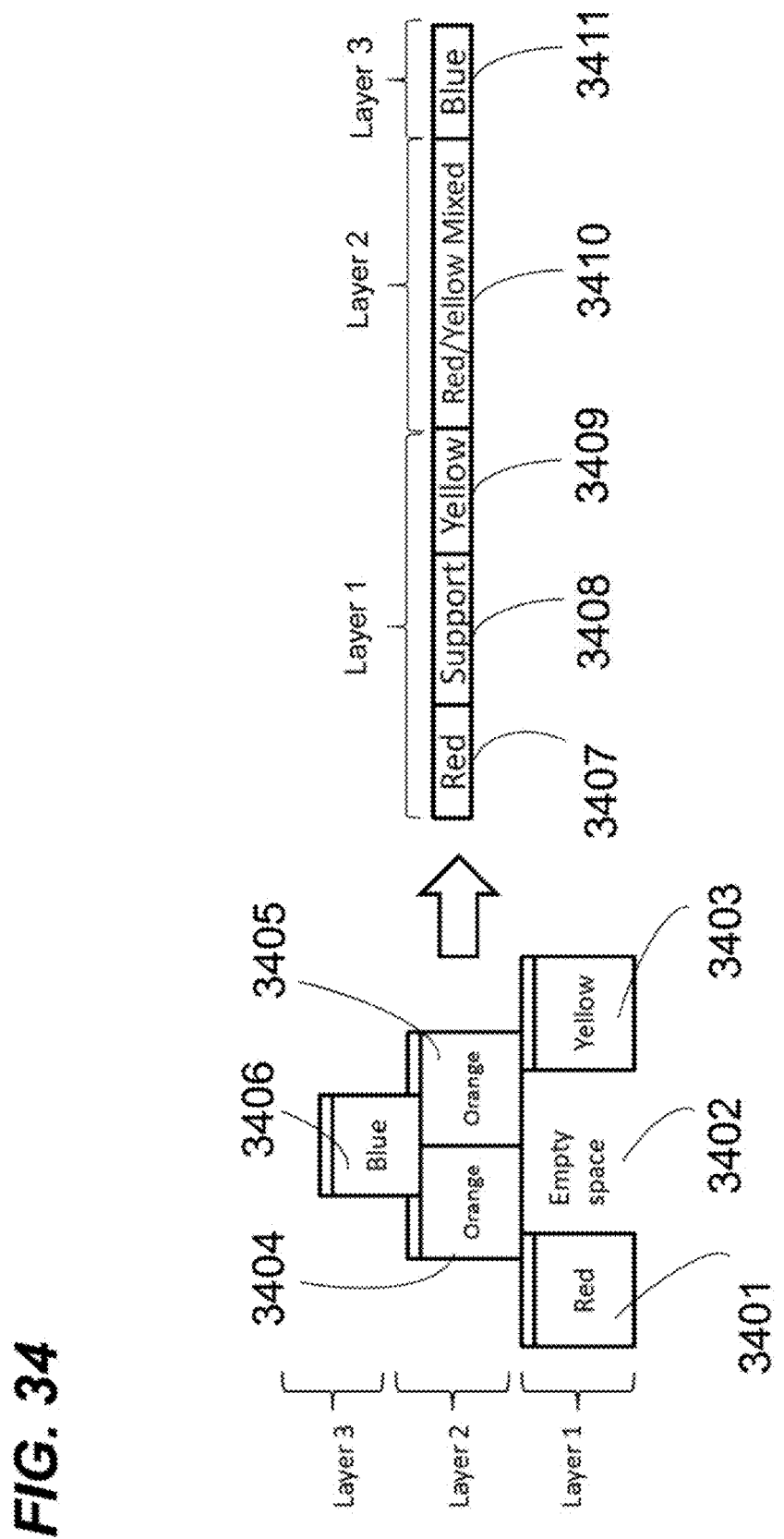
FIG. 34 is an embodiment of a method for creating an object using multiple materials using an additive manufacturing device.

FIG. 34 illustrates how an embodiment of the present invention may be used to improve the process by which a three dimensional fabricator functions. A computer rendering of an object that one desires to fabricate can be viewed as created in separate "voxels" or 3D (three dimension) pixels, with defined regions in x, y, z space.

Traditionally, a three dimensional fabricator can envision an object sliced into layers, such as in voxels 3401, 3402, 3403, 3404, 3405, and 3406 of FIG. 34. In this example, three layers are envisioned. The material deposition head can then be used to deposit each layer in succession until production of the desired object is completed. Materials are typically extruded in of a single uniform filament of single material and color. This is most easily visualized as a filament, though it could be a viscous fluid that provides similar results. Some devices may include a separate support material extruded through a separate deposition tip.

In an embodiment of the present invention, by contrast, the material filament is not uniform, but rather it can be created by combining several materials and/or colors. As shown in the example illustrated by FIG. 34, an embodiment of the invention may have red, yellow, blue and support material provided. Upon receiving a request to produce a desired object, depicted with voxels 3401, 3402, 3403, 3404, 3405, and 3406, a fabrication software application can be used devise various slices of layers (three in this example), and provide a control unit of the fabricator with a set of paths to follow in order to deposit material appropriately for each layer. Likewise, fabrication software application can also examine each layer and determine the appropriate material or material combination which should be deposited. For example, in the first layer desired voxels 3401, 3402, and 3403 would require material to be deposited according to a specific geometry and specific material composition, such that a rectangular layer is generated from a filament created using corresponding materials 3407, 3408, 3409, performed via the sequential deposition of these materials and colors. The second layer is composed of 3404 and 3405, but both are supposed to be orange, which is a color not included in the cartridges of this example. However, the device can provide mixture red and yellow 3410 to yield an orange deposition material. The third layer is composed of blue 3406 and requires a simple deposition of blue material 3411 from a cartridge of blue material that is available in this example. Support material 3408 can be removed (or dissolve on its own) to yield desired empty space in voxel 3402. An alternative embodiment of the present invention (which may or may not use a filament) can be practiced with a single color and/or material wherein one or more additives are combined in a mixing chamber to yield the desired material or color prior to deposition, in order to achieve production of an object with desired geometry, colors and materials.

It will be appreciated by persons of ordinary skill in the art that the present invention is not limited to the exemplary embodiments illustrated and described herein, nor is it limited to the dimensions or specific physical implementations illustrated and described herein. The present invention may have other embodiments that are readily apparent and enabled as a result of the concepts and descriptions provided herein.

What is claimed is:

1. A three dimensional fabricator comprising:
 a control unit for receiving instructions from a fabrication command unit and operating a material deposition tool head;
 a cartridge bay configured to receive material cartridges;
 a build surface configured to receive material deposited by the material deposition tool head;
 a first material heating chamber configured to receive a plurality of materials or colors from the cartridge bay, mix or fuse the plurality of materials or colors into a first mixture, and extrude the first mixture to the material deposition tool head for deposition on the build surface to form a three dimensional structure according to a prescribed order and prescribed pattern, wherein the material deposition tool head comprises a second material heating chamber and a deposition tip.

2. A fabricator of claim 1, wherein the first material heating chamber is configured to sequentially pass the first mixture and a second mixture of materials or colors to the material deposition tool head, such that deposition of the first mixture by the material deposition tool head is immediately followed by deposition of the second mixture.

3. A fabricator of claim 1, wherein the plurality of materials or colors are combined by the first material heating chamber to create a hybrid material or color, such that the hybrid material or color is deposited by the material deposition tool head.

4. A fabricator of claim 1, wherein the first material heating chamber mixes or fuses a pellet based material.

5. A fabricator of claim 1, wherein the first material heating chamber mixes or fuses a filament based material.

6. A fabricator of claim 1, wherein the first material heating chamber mixes or fuses a fluid based material.

7. A fabricator of claim 1, wherein the first material heating chamber mixes or fuses a material with a dye or a reactive agent.

8. A three dimensional fabricator comprising:
 a material deposition tool head comprising a first deposition tip that is mechanically or magnetically attached;
 a control unit for receiving instructions from a fabrication command unit and operating the material deposition tool head;
 a second non-identical deposition tip;
 a build surface for receiving material deposited by the material deposition tool head;
 wherein the control unit is configured to operate the material deposition tool head to mechanically or magnetically disengage the first deposition tip and mechanically or magnetically engage the second deposition tip without user interaction during fabrication of a three dimensional structure, to deposit material through at least two deposition tips onto the build surface and form the three dimensional structure according to a prescribed order and prescribed pattern.

9. A fabricator of claim 8, wherein the first and second deposition tips are physically attached to the material deposition tool head at the same time.

10. A fabricator of claim 8, wherein the first and second deposition tips are not physically attached to the deposition tool head at the same time.

11. A fabricator of claim 8 configured to store the first and second deposition tips in a controlled environment with regulated temperature.

12. A three dimensional fabricator comprising:
 a control unit for receiving instructions from a fabrication command unit and operating a material deposition tool head;
 a build surface for receiving material deposited by the material deposition tool head; and
 at least one deposition tip attached to the material deposition tool head with a portion of the tip being mechanically, electronically or magnetically adjustable without user interaction to modify the tip opening in shape or size during fabrication of a three dimensional structure according to a prescribed order and prescribed pattern.

* * * * *